United States Patent [19]
O'Reilly

[11] Patent Number: 6,086,883
[45] Date of Patent: Jul. 11, 2000

[54] EXTRACT FROM THE LEAVES OF *GINKGO BILOBA*

[75] Inventor: Joseph O'Reilly, County Cork, Ireland

[73] Assignee: Montana Limited, Little Island, Ireland

[21] Appl. No.: 08/916,792

[22] Filed: Aug. 25, 1997

Related U.S. Application Data

[63] Continuation of application No. 08/652,530, Jun. 3, 1996, abandoned.

[30] Foreign Application Priority Data

Dec. 3, 1993 [IE] Ireland ..................................... 930939

[51] Int. Cl.$^7$ ........................... A61K 35/78; A61K 31/70
[52] U.S. Cl. .......................................... 424/195.1; 514/27
[58] Field of Search ............................. 424/195.1; 514/27

[56] References Cited

U.S. PATENT DOCUMENTS

| | | | |
|---|---|---|---|
| 4,886,904 | 12/1989 | Tanaka et al. | 560/249 |
| 5,389,370 | 2/1995 | O'Reilly et al. | 424/195.1 |
| 5,512,286 | 4/1996 | Schwabe | 424/195.1 |

FOREIGN PATENT DOCUMENTS

| | | |
|---|---|---|
| 0324197 | 7/1989 | European Pat. Off. . |
| 0324197B1 | 7/1989 | European Pat. Off. . |
| 0330567 | 8/1989 | European Pat. Off. . |
| 0436129A1 | 7/1991 | European Pat. Off. . |
| 1767098 | 3/1968 | Germany . |
| 1767098 | 5/1972 | Germany . |
| 2117429B2 | 10/1972 | Germany . |
| 0067422 | of 1988 | Japan . |

OTHER PUBLICATIONS

O'Reilly Annual Proc. Phytochem. Soc. of Europe, 1993 pp. 253–270.

Database WPI Section Ch, Week 8810, Derwent Pub., Ltd., London GB, JP,A,63 021 061, Jan. 28, 1988.

Patent Abstracts of Japan, vol. 012, No. 139, Apr. 27, 1988 & JP,A,62 255 433, Nov. 7, 1987.

*Primary Examiner*—Leon B. Lankford, Jr.
*Assistant Examiner*—Christopher R. Tate
*Attorney, Agent, or Firm*—Jacobson, Price, Holman & Stern, PLLC

[57] ABSTRACT

Extracts of leaves of *Ginkgo biloba* contain at least 25% glycolipids by weight, preferably at least 1% cerebrosides including galactocerebroside. The extract has less than 50 ppm of ginkgolic acid. The extract is prepared by recovering a lipid fraction which is mixed with alcohol providing an alcoholic medium. The alcoholic medium is treated in a chromatographic column with a mixture of acetone and toluene to remove neutral lipids and ginkgolic acid, and subsequently the alcoholic solution in the column is further treated with a mixture of acetone and water to extract the glycolipids. The extracts have shown activity in cosmetic and skin care applications.

36 Claims, No Drawings

EXTRACT FROM THE LEAVES OF GINKGO BILOBA

This is a continuation of application Ser. No. 08/652,530, filed Jun. 3, 1996 which was abandoned upon the filing hereof.

The invention relates to a new extract from the leaves of *Ginkgo biloba* and its method of preparation.

Certain extracts from the leaves of *Ginkgo biloba* are widely used for the therapy of peripheral and cerebral arterial circulatory disturbances. Various processes for preparing such extracts are described for example in DE-B-1767098, DE-B 2117429, EP-A 0 324 197, EP-A 330 567 and EP-A 0 436 129.

According to one aspect of the invention there is provided an extract from the leaves of *Ginkgo biloba* containing at least 25% glycolipids by weight and less than 50 ppm of ginkgolic acids. In a preferred embodiment of the invention the extract further contains at least 1% by weight cerebrosides.

In one embodiment of the invention the extract contains at least 35% glycolipids, preferably approximately 40% glycolipids. In this case preferably the glycolipids comprise a mixture of monagalactodiglycerides, digalactodiglycerides and cerebrosides. Preferably the weight ratio of monogalactoaiglycerides to digalactodiglycerides is from 1:1 to 3:1, most preferably approximately 5:3.

In another embodiment of the invention the extract contains less than 50% glycolipids and cerebrosides. In this case preferably the extract contains from 30% to 45% glycolipids and cerebrosides. Preferably the glycolipids are predominantly digalactodiglycerides. In this case preferably the weight ratio of glycolipids to cerebrosides is from 2:1 to 6:1, most preferably approximately 4:1. Typically the cerebrosides include galactocerebroside which is preferably present in an amount of from 3% to 12%, most preferably 3% to 10% by weight.

The invention also provides a method for preparing a glycolipid extract from *Ginkgo biloba* leaves comprising the steps of:

extracting the leaves with an organic solvent;

separating the extract from the leaves;

cooling the extract to precipitate a lipid fraction;

recovering the lipid fraction from the extract;

mixing the lipid fraction with an alcohol;

removing insoluble material;

extracting the alcoholic solution;

treating the alcoholic solution with a first extracting medium to remove neutral lipids and ginkgolic acids;

treating the alcoholic solution with a second extracting medium to extract glycolipids;

purifying the second medium containing the glycolipids; and removing the second medium to provide a concentrated glycolipid extract.

Preferably the concentrated alcoholic solution is dissolved in an organic solvent and the solution is applied to a chromatographic column, the alcoholic solution being treated with the first extracting medium by passing the first medium through the column. Typically the first medium is an organic solvent, preferably a mixture of acetone and toluene.

Preferably the concentrated alcoholic solution is treated with the second extracting medium by passing the second medium through the column. Typically the second extracting medium is a mixture of an organic solvent and an alcohol, preferably a mixture of acetone and ethanol.

In one embodiment of the invention the organic solvent used to extract the leaves is acetone/water. Preferably after recovery from the extract the lipid fraction is washed and then further separated. Typically the alcohol with which the lipid fraction is mixed is ethanol.

In a preferred arrangement the medium containing the glycolipids is purified by treating with charcoal and filtering the treated extract to remove the charcoal.

Preferably the second medium is removed by evaporation.

In another aspect the constituents of the extract of the invention have a similar polarity to that of glycolipids.

The invention also provides a topical composition including an extract of the invention.

The invention will be more clearly understood from the following description thereof, given by way of example only.

In general terms in the process of the invention, the leaves of *Ginkgo biloba* are first extracted with an organic solvent such as acetone/water and the resulting solution is concentrated, for example, by evaporation and cooled. The solution is then filtered and a $C_1$–$C_3$ alcohol such as ethanol is added to the precipitate. The solution is agitated and again filtered. The filtrate is adjusted with water and may be extracted with a suitable solvent such as petroleum spirit and/or hexane/heptane. The aqueous alcoholic phase is then evaporated to dryness and an organic solvent, preferably acetone/toluene, is added.

In one embodiment of the invention the organic solvent is a 5% to 30%, most preferably 15% acetone/solvent mixture.

In another embodiment of the invention the organic solvent is a 40% to 60%, most preferably 50% acetone/solvent mixture.

The resulting solution is filtered, typically concentrated, and then purified by chromatographic separation using a first medium, typically acetone/toluene. The glycolipid fraction is removed using a second medium typically comprising acetone/ethanol. The glycolipid fraction is then purified, for example by treating with charcoal, filtered to remove the charcoal, and then evaporated for complete removal of the acetone/toluene solvents.

The invention also provides an extract in which the constituents have a similar polarity to that of the glycolipids.

The process will be described in further detail in the is following Examples.

EXAMPLE 1

Step 1

100 kg of finely milled *Ginkgo biloba* leaves were extracted with 800 l of a 60% acetone water mixture in a counter current extraction unit at a temperature of 55–60° C.

The extract was separated from the leaves and was then concentrated by evaporation.

Step 2

The concentrate was cooled to 8–10° C. and was retained at this temperature for 3 hours.

The lipids which precipitated were recovered by decanting.

The recovered lipids were then dissolved in an agitated solution of 2.9 kg of acetone and 0.7 kg of demineralised water. A further 30 kg of demineralised water was then added.

The solution was continuously agitated and cooled to 8–10° C. and was retained for a minimum of 3 hours before being decanted.

Step 3

The wet decanted lipids from Step 2 were added to 200 kg of ethanol and agitated for 60 minutes.

Insoluble material was removed by decanting.

Step 4

The ethanolic solution from Step 3 was adjusted to 12–15% water.

The solution was extracted twice with 140 l of petroleum distillate (boiling range 60–80° C.).

The ethanol-water phase was evaporated to greater than 85% dry extract.

Step 5

The extract from Step 4 was dissolved in 15% acetone/toluene.

This solution was filtered and was then applied to 30 kg of silica in a packed column. 800 l of 15% acetone/toluene were pumped through the columns. The column was then flushed with 200 l of 7.5% ethanol/acetone.

Step 6

The ethanol/acetone fraction was purified by addition of 1.1 kg Charcoal to the ethanol/acetone fraction and the solution was agitated for 30 minutes.

The solution was filtered and the solvent removed by evaporation.

0.98 kg of a green brown oil having the following characteristics are obtained:

| Glycolipids | 40% |
| consisting of Monogalactodiglycerides | 25% and |
| Digalactodiglycerides | 15% |
| Ginkgolic Acids | 39 ppm |
| Galactocerebroside | 6% |

EXAMPLE 2

Step 1

70 kg of finely milled *Ginkgo biloba* leaves were extracted with 560 l of a 60% acetone water mixture in a counter current extraction unit at a temperature of 55–60° C.

The extract was separated from the leaves and was then evaporated to reduce the acetone content to less than 3%.

Step 2

The concentrate was cooled to 8–10° C. and was retained at this temperature for 3 hours The lipids which precipitated were recovered by decanting.

The recovered lipids were then dissolved in an agitated solution of 2.0 kg of acetone. A further 20 kg of demineralised water was then added.

The solution was continuously agitated and cooled to 8–10° C. and was retained for a minimum of 3 hours before being decanted.

Step 3

The wet decanted lipids from Step 2 were added to 30 kg of methanol and agitated for 60 minutes.

Insoluble material was removed by decanting. The filtrate was evaporated to remove methanol.

Step 4

10 kg of acetone was added to the concentrate from Step 3 and agitated for 1 hour. The resulting solution was filtered and the filtrate evaporated.

Step 5

The extract from Step 4 was dissolved in 15% acetone/toluene.

This solution was filtered and was then applied to 8.5 kg of silica in a packed column. 60 l of 15% acetone/toluene were pumped through the columns. The column was then flushed with 17 l of 7.5% ethanol/toluene.

Step 6

0.24 kg of Charcoal was added to the ethanol/acetone fraction and the solution was agitated for 30 minutes.

The solution was filtered and the solvent removed by evaporation.

0.19 kg of a green brown oil having the following characteristics are obtained:

| Glycolipids | 27% |
| consisting of Monogalactodiglycerides | 20% and |
| Digalactodiglycerides | 7% |
| Ginkgolic Acids | 30 ppm |
| Galactocerebroside | 3.5% |

EXAMPLE 3

Step 1

70 kg of finely milled *Ginkgo biloba* leaves were extracted in with 600 l of a 60% acetone water mixture in a counter current extraction unit at a temperature of 55–60° C.

The extract was separated from the leaves and was then concentrated by evaporation.

Step 2

The concentrate was cooled to 8–10° C. and was retained at this temperature for a minimum 3 hours.

The lipids which precipitated were recovered by decanting.

The recovered lipids were then dissolved in an agitated solution of 2.2 kg of acetone and 0.5 kg of demineralised water. A further 22 kg of demineralised water was then added.

The solution was continuously agitated and cooled to 8–10° C. and was retained for a minimum of 3 hours before being decanted.

Step 3

The wet decanted lipids from Step 2 were added to 55 kg of ethanol and agitated for 60 minutes.

Insoluble material was removed by decanting.

The ethanol-water phase was evaporated to greater than 85% dry extract.

Step 4

The extract from

Step 3 was dissolved in 50% acetone/toluene.

This solution was filtered and was then applied to 18.5 kg of silica in a packed column. 150 l of 50% acetone/toluene were pumped through the columns. The column was then flushed with 100 l of 7.5% ethanol/acetone.

Step 5

The solution was concentrated and rechromotographed as above.

The ethanol/acetone fraction was purified by addition of 0.06 kg Charcoal to the ethanol/acetone fraction and the solution was agitated for 30 minutes.

The solution was filtered and the solvent removed by evaporation.

0.26 kg of a green brown paste having the following characteristics are obtained:

| Glycolipids | 33% |
| consisting of Monogalactodiglycerides | 1% and |
| Digalactodiglycerides | 31% |
| Ginkgolic Acids | not detected |
| Galactocerebroside | 10% |

EXAMPLE 4

Step 1

5 kg of finely milled *Ginkgo biloba* leaves were extracted with 40 l of a 60% acetone water mixture in a counter current extraction unit at a temperature of 50–60° C.

The extract was separated from the leaves and was then evaporated to reduce the acetone content to less than 3%.

Step 2

The concentrate was cooled to 8–10° C. and was retained at this temperature for 3 hours.

The lipids which precipitated were recovered by decanting.

The recovered lipids were dissolved in an agitated solution of 0.15 kg of acetone. A further 1.5 kg of demineralised water was then added.

The solution was continuously agitated and cooled to 8–10° C. and was retained for a minimum of 3 hours before being decanted.

Step 3

The wet decanted lipids from Step 2 were added to 2 kg of methanol and agitated for 60 minutes.

Insoluble material was removed by decanting. The filtrate was evaporated to remove methanol.

Step 4

0.5 kg of acetone was added to the concentrate from Step 3 and agitated for 1 hour. The resulting solution was filtered and the filtrate evaporated.

Step 5

The extract from Step 4 was dissolved in 20% acetone/toluene.

This solution was filtered and was then applied to 0.8 kg of silica in a packed column. 5.5 l of 20% acetone/toluene were pumped through the columns. The column was then flushed with 1.6 l of ethanol.

Step 6

25 g of Charcoal was added to the ethanol fraction and the solution was agitated for 30 minutes.

The solution was filtered and the solvent removed by evaporation.

19 g of a green brown oil having the following characteristics are obtained:

| | |
|---|---|
| Glycolipids | 42% |
| consisting of Monogalactodiglycerides | 29% |
| Digalactodiglycerides | 13% |
| Galactocerebroside | 3% |

It will be appreciated that while the extracts have been characterised as containing glycolipids it may be possible that the major constituents have a polarity similar to that of glycolipids.

The extracts have shown activity in cosmetic and skin care applications.

The invention is not limited to the specific embodiments hereinbefore described, which may be varied in detail.

We claim:

1. An extract from the leaves of *Ginkgo biloba* comprising at least 25% of glycolipids by weight and less than 50 ppm of ginkgolic acids.

2. The extract as claimed in claim 1 further comprising at least 1% by weight cerebrosides.

3. The extract as claimed in claim 1 comprising at least 35% glycolipids.

4. The extract as claimed in claim 1 comprising approximately 40% glycolipids.

5. The extract as claimed in claim 1 wherein the glycolipids comprise a mixture of monogalactodiglycerides and diagalactodiglycerides.

6. The extract as claimed in claim 5 wherein the weight ratio of monogalactodiglycerides to digalactodiglycerides is from 1:1 to 3:1.

7. The extract as claimed in claim 5 wherein the weight ratio of monogalactodiglycerides to digalactodiglycerides is approximately 5:3.

8. The extract as claimed in claim 1 wherein the extract further comprises cerebrosides and the combined amount of said cerebrosides and glycolipids is less than 50% by weight.

9. The extract as claimed in claim 8 wherein the extract comprises from 30% to 45% glycolipids and cerebrosides by weight.

10. The extract as claimed in claim 8 wherein the glycolipids are predominantly digalactodiglycerides.

11. The extract as claimed in claim 8 wherein the ratio of glycolipids to cerebrosides is from 2:1 to 6:1.

12. The extract as claimed in claim 11 wherein the ratio of glycolipids to cerebrosides is approximately 4:1.

13. The extract as claimed in claim 8 wherein the cerebrosides include galactocerebroside.

14. The extract as claimed in claim 13 wherein the galactocerebroside is present in an amount of from 3% to 12% by weight.

15. The extract as claimed in claim 13 wherein the galactocerebroside is present in an amount of from 3% to 10% by weight.

16. The extract as claimed in claim 1, further comprising constituents having a similar polarity to that of glycolipids.

17. An extract from the leaves of *Ginkao biloba* comprising 25% by weight of monogalactodiglycerides, 15% by weight digalactodiglycerides, 6% by weight cerebrosides and less than 50 ppm ginkgolic acids.

18. An extract from the leaves of *Ginkgo biloba* comprising 20% by weight of monogalactodiglycerides, 7% by weight digalactodiglycerides, 3.5% by weight cerebrosides and less than 50 ppm ginkolic acids.

19. An extract from the leaves of *Ginkgo biloba* comprising 1% by weight monogalactodiglycerides, 31% by weight digalactodiglycerides, 10% by weight cerebrosides and less than 50 ppm ginkgolic acids.

20. An extract from the leaves of *Ginkgo biloba* containing 29% by weight monogalactodiglycerides, 13% by weight digalactodiglycerides, 3% by weight cerebrosides and less than 50 ppm ginkolic acids.

21. A method for preparing a glycolipid extract from *Ginkgo biloba* comprising the steps of:

(a) extracting the leaves with an alcohol or a ketone;

(b) separating the extract from the leaves;

(c) concentrating the extract by evaporation;

(d) cooling the extract to precipitate a lipid fraction;

(e) recovering the lipid fraction from the extract;

(f) dissolving the recovered lipids in a ketone and reprecipitating;

(g) mixing the lipid fraction with a short chain alcohol;

(h) removing insoluble material;

(i) extracting the alcoholic solution with an alkane to remove neutral lipids and ginkgolic acids;

(j) concentrating the alcoholic solution by evaporation;

(k) treating the concentrated alcoholic solution with a first extracting organic solvent to remove neutral lipids and ginkgolic acids;

(l) treating the concentrated alcoholic solution with a second extracting mixture of an organic solvent and an alcohol to extract glycolipids;

(m) purifying the second extracting mixture of an organic solvent and an alcohol containing the glycolipids;

(n) removing the second extracting mixture of an organic solvent and an alcohol to provide a concentrated glycolipid extract; and (o) recovering the glycolipid extract.

22. The method as claimed in claim 21 wherein the concentrated alcoholic solution is dissolved in an organic solvent and the solution is applied to a chromatographic column, the alcoholic solution being treated in step k with the first extracting organic solvent by passing the first extracting organic solvent through the column.

23. The method as claimed in claim 22 wherein the concentrated alcoholic solution is treated with the second extracting mixture of the organic solvent and the alcohol by passing the second extracting mixture of the organic solvent and the alcohol through the column.

24. The method of claim 23 wherein the second extracting mixture of the organic solvent and alcohol is a mixture of acetone and ethanol.

25. The method as claimed in claim 21 wherein the first extracting organic solvent is a mixture of acetone and toluene.

26. The method as claimed in claim 21 wherein the first extracting organic solvent is 5–30% acetone/toluene.

27. The method as claimed in claim 21 wherein the first extracting organic solvent is 15% acetone/toluene.

28. The method as claimed in claim 21 wherein the first extracting organic solvent is 40% to 60% acetone/toluene.

29. The method as claimed in claim 21 wherein the first extracting organic solvent is 50% acetone/toluene.

30. The method as claimed in claim 21 wherein the ketone or alcohol used to extract the leaves is a mixture of acetone and water or alcohol and water.

31. The method as claimed in claim 21 wherein after recovery of the lipid fraction, the lipid fraction is washed and then further separated.

32. The method as claimed in claim 21 wherein the short chain alcohol with which the lipid fraction is mixed is ethanol.

33. The method as claimed in claim 21 wherein the second extracting mixture of the organic solvent and the alcohol containing the glycolipids is purified by treating with charcoal and filtering the treated extract to remove the charcoal.

34. The method as claimed in claim 21 wherein the second extracting mixture of the organic solvent and the alcohol is removed by evaporation.

35. A glycolipid extract from *Ginkgo biloba* leaves obtained by the method as claimed in claim 21.

36. A topical composition comprising a glycolipid extract from *Ginkgo biloba* leaves, obtained by the method as claimed in claim 21.

* * * * *